United States Patent [19]

Ueda et al.

[11] Patent Number: 4,563,453
[45] Date of Patent: Jan. 7, 1986

[54] THIAZINE DERIVATIVES, PROCESSES FOR PREPARATION THEREOF AND PHARMACEUTICAL COMPOSITION COMPRISING THE SAME

[75] Inventors: Ikuo Ueda, Toyonaka; Masayuki Kato, Osaka; Yosiharu Kasai, Daito, all of Japan

[73] Assignee: Fujisawa Pharmaceutical Co., Ltd., Osaka, Japan

[21] Appl. No.: 658,683

[22] Filed: Oct. 9, 1984

[30] Foreign Application Priority Data

Oct. 17, 1983 [GB] United Kingdom ............... 8327735
Sep. 5, 1984 [GB] United Kingdom ............... 8422420

[51] Int. Cl.$^4$ ............... C07D 513/04; C07D 513/14; A61K 31/54
[52] U.S. Cl. ............... 514/222; 544/33; 544/48
[58] Field of Search ............ 514/222; 544/48, 33

[56] References Cited

U.S. PATENT DOCUMENTS

| | | | |
|---|---|---|---|
| 3,591,584 | 7/1971 | Lombardino et al. | 260/243 |
| 4,076,709 | 2/1978 | Hromatka et al. | 544/48 |
| 4,137,313 | 1/1979 | Trummlitz et al. | 544/33 |
| 4,224,445 | 9/1980 | Hromatka et al. | 544/48 |
| 4,259,336 | 3/1981 | Engel et al. | 544/33 |
| 4,348,519 | 9/1982 | Pfister | 544/33 |

*Primary Examiner*—John M. Ford

*Attorney, Agent, or Firm*—Oblon, Fisher, Spivak, McClelland & Maier

[57] ABSTRACT

New thiazine derivatives of the formula:

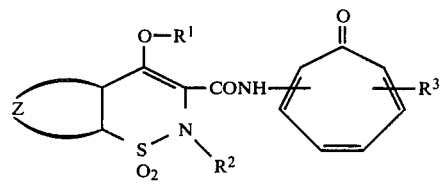

wherein
- $R^1$ is hydrogen or acyl,
- $R^2$ is hydrogen or lower alkyl,
- $R^3$ is hydrogen, hydroxy, halogen, lower alkyl or lower alkoxy,
- Z is taken together with the adjacent carbon atoms to form an unsaturated heterocyclic ring which may be substituted with phenyl, halogen, acyl or lower alkyl, and
- the heavy solid line means single or double bond, and pharmaceutically acceptable salts thereof, and processes for preparation thereof and pharmaceutical composition comprising the same.

These derivatives and salts thereof are useful as antiinflammatory, analgesic and antirheumatic agents.

12 Claims, No Drawings

THIAZINE DERIVATIVES, PROCESSES FOR PREPARATION THEREOF AND PHARMACEUTICAL COMPOSITION COMPRISING THE SAME

The present invention relates to novel thiazine derivatives. More particularly, it relates to novel thiazine derivatives which have antiinflammatory, analgesic and antirheumatic activities, to processes for preparation thereof, to pharmaceutical composition comprising the same, and to methods of using the same therapeutically in the treatment of inflammation, various pains and rheumatism in human beings and animals.

Accordingly, one object of this invention is to provide novel thiazine derivatives which are useful as antiinflammatory, analgesic and antirheumatic agents.

Another object of this invention is to provide processes for preparation of said thiazine derivatives.

A further object of this invention is to provide pharmaceutical composition comprising, as an active ingredient, said thiazine derivative.

Still further object of this invention is to provide a method of using said thiazine derivatives in the treatment of inflammation, various pains and rheumatism in human being and animals.

Some thiazine derivatives having antiinflammatory activity have been known as described, for example, in U.S. Pat. No. 3,591,584 and No. 4,076,709.

The object thiazine derivatives are novel and can be represented by the following general formula [I]:

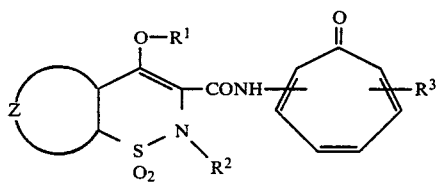

wherein
R[1] is hydrogen or acyl,
R[2] is hydrogen or lower alkyl,
R[3] is hydrogen, hydroxy, halogen, lower alkyl or lower alkoxy,
Z is taken together with the adjacent carbon atoms to form an unsaturated heterocyclic ring which may be substituted with phenyl, halogen, acyl or lower alkyl, and
the heavy solid line means single or double bond.

As to the object compound [I], the following points are to be noted. That is, when R[1] is hydrogen, the object compound can be alternatively represented by its tautomers as shown in the following.

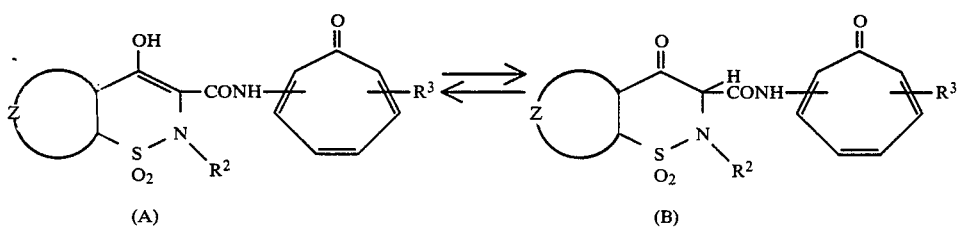

wherein R[2], R[3], Z and the heavy solid line are each as defined above.

In the present specification and claim, however, the object compound of this invention is represented by the formula (A) only for the convenient sake.

The object compound [I] and its salt can be prepared by the following processes.

Process 1

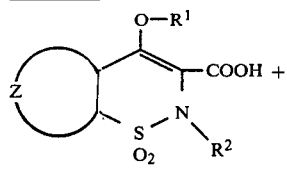

[II]
or its reactive derivative
at the carboxy group
or a salt thereof

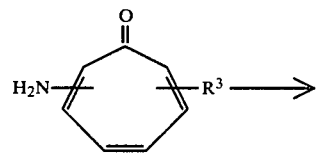

[III]
or its reactive derivative
at the amino group
or a salt thereof

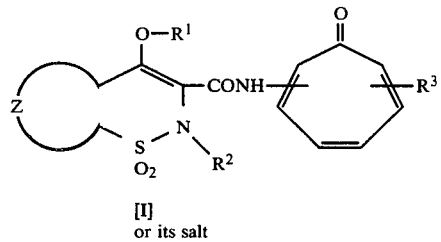

[I]
or its salt

Process 2

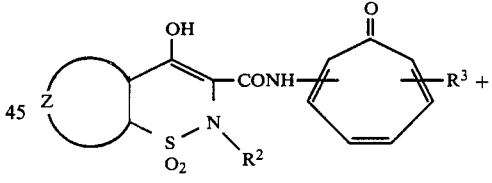

[Ia]
or its salt

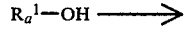

[IV]
or its reactive derivative
at the carboxy group or
a salt thereof

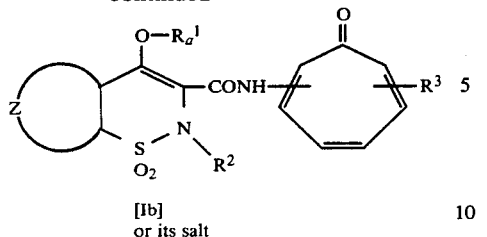

[Ib] or its salt

Process 3

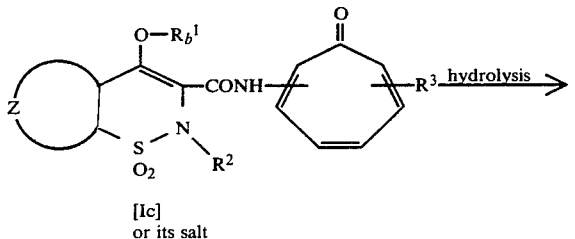

[Ic] or its salt

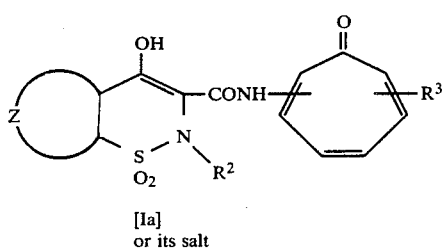

[Ia] or its salt wherein $R^1$, $R^2$, $R^3$, Z and the heavy solid line are each as defined above, and $R_a{}^1$ and $R_b{}^1$ are each acyl.

In the above and subsequent description of the present specification, suitable examples and illustrations for the various definitions to be included within the scope of the invention are explained in detail as follows:

The term "lower" is intended to mean a group having 1 to 6 carbon atom(s), unless otherwise provided.

Suitable examples of acyl for $R^1$, $R_a{}^1$ and $R_b{}^1$ may be lower alkanoyl [e.g. formyl, acetyl, propionyl, hexanoyl, etc.], aroyl [e.g. benzoyl, naphthoyl, etc.], ar(lower)alkenoyl [e.g. cinnamoyl, etc.], or the like.

Suitable examples of lower alkyl for $R^2$ and $R^3$ may be a straight or branched one such as methyl, ethyl, propyl, isopropyl, butyl, isobutyl, t-butyl, pentyl, hexyl or the like.

Suitable examples of lower alkoxy for $R^3$ may be methoxy, ethoxy, propoxy, isopropoxy, butoxy, t-butoxy, pentyloxy, hexyloxy or the like.

Suitable examples of halogen for $R^3$ include chlorine, bromine, iodine and fluorine.

The unsaturated heterocyclic ring for Z may include unsaturated monocyclic and polycyclic rings containing at least one hetero-atom consisting of oxygen, sulfur and nitrogen atoms. Suitable examples of said unsaturated heterocyclic ring may be unsaturated, 5- or 6-membered monocyclic heterocyclic ring [e.g. furan, thiophene, pyrrole, imidazole, pyridine, etc.], unsaturated fused heterocyclic ring [e.g. benzofuran, benzothiophene, indole, quinoline, etc.], or the like. These unsaturated heterocyclic rings may be optionally substituted with phenyl, halogen, acyl or lower alkyl as exemplified before.

Suitable examples of the unsaturated heterocyclic ring having such substituent(s) may be lower alkyl substituted one [e.g. 3-methylthiophene, 5-methylbenzothiophene, 4-ethylbenzothiophene, etc.], phenyl substituted one [e.g. 3-phenylthiophene, etc.], halogenated one [e.g. 3-chlorothiophene, 5-chlorobenzothiophene, etc.], acylated one [e.g. 3-acetylthiophene, etc.], or the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, or organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate, trifluoroacetate, maleate, tartrate, methanesulfonate, benzensulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], and the like.

In this respect, it is to be noted that the compounds [Ia], [Ib] and [Ic] are included within the scope of the compound [I], and accordingly the suitable salts of these compounds [Ia], [Ib] and [Ic] are to be referred to those as exemplified for the object compound [I].

The processes for preparing an object compound [I] and its salt are explained in detail in the following.

PROCESS 1

The object compound [I] and its salt can be prepared by reacting a compound [II] or its reactive derivative at the carboxy group or a salt thereof with a compound [III] or its reactive derivative at the amino group or a salt thereof.

Suitable reactive derivatives at the carboxy group of the compound [II] may include an acid halide, an acid anhydride, an ester, an activated amide and the like.

Suitable examples of such reactive derivatives may be an ester such as lower alkyl ester [e.g. methyl ester, ethyl ester, propyl ester, hexyl ester, etc.] or an activated ester with N-hydroxysuccinimide, N-hydroxyphthalimide or 1-hydroxy-6-chlorobenzotriazole, an acid chloride, an acid bromide, an acid azide, a mixed acid anhydride with an acid such as substituted phosphoric acid [e.g. dialkylphosphoric acid, phenylphosphoric acid, etc.], aliphatic carboxylic acid [e.g. pivalic acid, acetic acid, trichloroacetic acid, etc.] or the like, a symmetrical acid anhydride, an activated amide with imidazole triazole or dimethylpyrazole, or the like.

Suitable reactive derivatives at the amino group of the compound [III] include conventional ones used in amidation, for example, Schiff's base type imino or its tautomeric enamine type isomer formed by reaction of the compound [III] with a carbonyl compound, a silyl derivative formed by reaction of the compound [III] with a silyl compound such as trimethylsilylacetamide, bis(trimethylsilyl) acetamide or the like, a derivative formed by reaction of the compound [II] with phosphorus trichloride or phosgene, and the like.

The reactive derivatives of the compounds [II] and [III] can be selected according to the kinds of the compounds [II] and [III], respectively.

Suitable salts of the compounds [II] and [III] and their reactive derivatives may be the same as those exemplified for the compound [I].

When the compound [II] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction is usually carried out in a conventional solvent such as water, acetone, dioxane, chloroform, methylene chloride, ethylene chloride, tetrahydrofuran, benzene, toluene, xylene, ethyl acetate, N,N-dimethylformamide, pyridine or any other organic solvent which does not adversely influence the reaction. Among these solvents, hydrophilic solvents may be used in a mixture with water.

The reaction may be preferably carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base or the condensing agent to be used is liquid, it can also be used as a solvent.

The reaction temperature is not critical, and the reaction can be carried out under cooling, at ambient temperature or under warming or heating.

PROCESS 2

The object compound [Ib] and its salt can be prepared by reacting a compound [Ia] or its salt with a compound [IV] or its reactive derivative at the carboxy group or a salt thereof.

Suitable reactive derivatives at the carboxy group of the compound [IV] may be the same as those exemplified for the compound [II].

Suitable salts of the compound [IV] and its reactive derivative at the carboxy group may be the same as those exemplified for the compound [I].

This reaction can be carried out substantially in the same manner as that of Process 1, and therefore the reaction mode and reaction conditions [e.g. condensing agent, base, solvent, reaction temperature, etc.] of this process are to be referred to those as explained in Process 1.

Process 3

The object compound [Ia] and its salt can be prepared by hydrolyzing the compound [Ic] or its salt.

This reaction is usually carried out in the presence of an acid or a base.

Suitable acid includes an inorganic acid [e.g. hydrochloric acid, hydrobromic acid, sulfuric acid, etc.], an organic acid [e.g. formic acid, acetic acid, trifluoroacetic acid, propionic acid, benzensulfonic acid, p-toluenesulfonic acid, etc.], an acidic ion exchange resin and the like.

Suitable base includes an inorganic base such as alkali or alkaline earth metal hydroxide or the corresponding carbonate or bicarbonate [e.g. sodium hydroxide, potassium hydroxide, sodium carbonate, potassium carbonate, lithium carbonate, sodium bicarbonate, calcium hydroxide, magnesium hydroxide, etc.], ammonium hydroxide or the like; an organic base such as an alkoxide or phenoxide of the above metal [e.g. sodium methoxide, sodium ethoxide, potassium t-butoxide, sodium phenoxide, lithium phenoxide, etc.], an amine such as mono-, di- or trialkylamine [e.g. methylamine, ethylamine, propylamine, isopropylamine, butylamine, N,N'-dimethyl-1,3-propanediamine, trimethylamine, triethylamine, etc.], unsubstituted mono- or disubstituted arylamine [e.g. aniline, N-methylaniline, N,N-dimethylaniline, etc.], a heterocyclic base [e.g. pyrrolidine, morpholine, N-methylmorpholine, N-methylpiperidine, N,N'-dimethylpiperazine, pyridine, etc.], hydrazines [e.g. hydrazine, methylhydrazine, ethylhydrazine, etc.] or the like; a basic ion-exchange resin and the like.

This reaction is usually carried out in a solvent which does not adversely influence the reaction such as water, hydrophilic solvent such as alcohol [e.g. methanol, ethanol, propanol, etc.], acetone, N,N-dimethylformamide, tetrahydrofuran, dioxane, dimethyl sulfoxide, etc. or a mixture thereof, and other hydrophobic solvent such as benzene, diethyl ether, etc. may also be used as a solvent. In case that the acid or base to be used in this reaction is liquid, it can also be used as a solvent.

The reaction temperature is not critical, and the reaction is usually carried out at ambient temperature or under warming or heating.

The compounds [I], [Ia] and [Ib] can be isolated and purified by a conventional manner such as recrystallization, column chromatography, reprecipitation or the like.

It is to be noted the compounds [I], [Ia], [Ib], [Ic], [II], [III] and [IV] may include one or more stereoisomers due to asymmetric carbon atoms and all of such isomers are included within the scope of this invention.

Among the starting compound [II], new compounds may be obtained by any process known in the art for preparing structurally analogous compound thereto.

The new thiazine derivatives [I] and pharmaceutically acceptable salts thereof posses antiinflammatory, analgesic and antirheumatic activities, and are useful for a therapeutic treatment of inflammation, various pains [e.g. headache, toothache, menorrhalgia, etc.] and rheumatism.

For therapeutic purpose, the compounds according to the present invention can be used in a form of pharmaceutical preparation containing one of said compounds, as an active ingredient, in admixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in the above preparations, auxiliary substances, stabilizing agents, wetting or emulsifying agents, buffers and other commonly used additives.

While the dosage of the compounds will vary depending upon the age and condition of the patient, an average single dose of about 0.1 mg, 1 mg, 10 mg, 50 mg, 100 mg, 250 mg, 500 mg and 1000 mg of the compounds according to the present invention may be effective for treating inflammation, various pains and rheumatism. In general, amounts between 0.1 mg/body and about 1,000 mg/body or even more may be administered per day.

In order to illustrate the usefulness of the object compound [I], the pharmacological test data of the representative compounds of the object compounds [I] are shown below.

TEST A (Carrageenin foot edema)

(1) Test Method:

Male Sprague-Dawley rats weighing about 200 g were used in groups of five. Paw edema was induced by subplantar injection of 1% carrageenin (0.1 ml/rat) into the right hind paw. The test drug was suspended in 0.5% methylcellulose and administered orally 60 minutes before phlogogen. Paw volume was measured with plethysmometer (Ugo Basil Co., Ltd.) by water displacement immersing the paw to the lateral malleolus. The difference of paw volume before and 3 hours after the phlogogen was designated as edema volume. The data was analyzed statistically by student's t-test.

(2) Test Compounds:

(a) 4-Hydroxy-2-methyl-N-(1-oxo-2,4,6-cycloheptatrien-2-yl)-2H-thieno[2,3-e]-1,2-thiazine-3-carboxamide 1,1-dioxide.

(b) 4-Hydroxy-2-methyl-N-(1-oxo-2,4,6-cycloheptatrien-2-yl)-2H-[1]benzothieno[2,3-e]-1,2-thiazine-3-carboxamide 1,1-dioxide.

(3) Test Results:

| Test Compound | Dose (mg/kg) | Inhibition (%) |
| --- | --- | --- |
| (a) | 10.0 | 63.6 |
| (b) | 10.0 | 34 |

TEST B (Arthus foot edema)

(1) Test Method:

Five male Sprague-Dawley rats weighing about 200 g were used per group.

Paw edema was induced by intravenous injection of egg albumin (0.5 mg/rat) and subplantar injection of anti egg albumin antiserum (0.1 ml/rat) in Arthus type foot edema. The test drug was suspended in methylcellulose and administered orally 60 minutes before phlogogen. Paw volume was measured with plethysmometer (Ugo Basil Co., Ltd.) by water displacement immersing the paw to the lateral malleolus. The difference of paw volume before and 3 hours after the phlogogen was designated as edema volume. The data were analyzed statistically by student's t-test.

(2) Test Compound:

4-Hydroxy-2-methyl-N-(2-hydroxy-1-oxo-2,4,6-cycloheptatrien-5-yl)-2H-thieno[2,3-e]-1,2-thiazine-3-carboxamide 1,1-dioxide.

(3) Test Result:

| Dose (mg/kg) | Inhibition (%) |
| --- | --- |
| 100 | 37.8 |

The following examples are given for the purpose of illustrating the present invention in more detail.

EXAMPLE 1

A solution of 3-ethoxycarbonyl-4-hydroxy-2-methyl-2H-thieno[2,3-e]-1,2-thiazine, 1,1-dioxide (0.27 g) and 2-aminotropone (0.124 g) in xylene (6 ml) was refluxed for 10 hours and the reaction mixture was allowed to stand at ambient temperature overnight.

The crystalline precipitates were collected by filtration and washed with toluene to give 4-hydroxy-2-methyl-N-(1-oxo-2,4,6-cycloheptatrien-2-yl)-2H-thieno[2,3-e]-1,2-thiazine-3-carboxamide 1,1-dioxide (0.3 g).

mp: 242°–245° C.

IR (Nujol): 3220, 1615, 1560, 1510 cm$^{-1}$

Analysis Calcd. for $C_{15}H_{12}N_2O_5S_2$: Calcd.: C, 49.44; H, 3.32; N, 7.69. Found: C, 49.17; H, 3.34; N, 7.68.

EXAMPLE 2

A solution of 4-hydroxy-3-methoxycarbonyl-2-methyl-2H-thieno[2,3-e]-1,2-thiazine, 1,1-dioxide (1.0 g) and 2-amino-5-chlorotropone (0.62 g) in xylene (25 ml) was refluxed for 21 hours and the reaction mixture was allowed to stand at ambient temperature.

The crystalline precipitates were collected by filtration and washed twice with toluene to give 4-hydroxy-2-methyl-N-(5-chloro-1-oxo-2,4,6-cycloheptatrien-2-yl)-2H-thieno[2,3-e]-1,2-thiazine-3-carboxamide 1,1-dioxide (1.22 g).

mp: 243°–245° C.

IR (Nujol): 3260, 1645, 1605, 1560, 1510, 1350 cm$^{-1}$

Analysis Calcd. for $C_{15}H_{11}ClN_2O_5S_2$: Calcd.: C, 45.17; H, 2.78; N, 7.02. Found: C, 45.07; H, 3.01; N, 7.04.

EXAMPLE 3

A solution of 4-hydroxy-3-methoxycarbonyl-2-methyl-2H-thieno[2,3-e]-1,2-thiazine 1,1-dioxide (1.0 g) and 5-amino-2-hydroxytropone (0.55 g) in xylene (25 ml) was refluxed for 21 hours and the reaction mixture was allowed to stand at ambient temperature. The crystals were collected by filtration, washed with toluene and recrystallized from N,N-dimethylformamide to give 4-hydroxy-2-methyl-N-(2-hydroxy-1-oxo-2,4,6-cycloheptatrien-5-yl)-2H-thieno[2,3-e]-1,2-thiazine-3-carboxamide 1,1-dioxide (0.82 g).

mp: 231°–232° C.

IR (Nujol): 3600, 3350, 3250, 1645, 1605, 1530, 1200 cm$^{-1}$

NMR (NaOD+$D_2O$+$CD_3OD$, δ): 3.00 (3H, s), 7.0–7.8 (6H, m)

Analysis Calcd. for $C_{15}H_{12}N_2O_6S_2 \cdot 0.5H_2O$: Calcd.: C, 46.27; H, 3.62; N, 7.19. Found: C, 46.16; H, 3.63; N, 7.31.

EXAMPLE 4

A solution of 4-hydroxy-3-methoxycarbonyl-2-methyl-2H-[19-benzothieno[2,3-e]-1,2-thiazine 1,1-dioxide (1.2 g) and 2-aminotropone (0.5 g) in xylene (30 ml) was refluxed for 24 hours. The resultant insoluble materials were filtered off immediately and the filtrate was allowed to stand at ambient temperature.

The crystalline precipitates were collected by filtration, washed with xylene and recrystallized from chloroform to give 4-hydroxy-2-methyl-N-(1-oxo-2,4,6-cycloheptatrien-2-yl)-2H-[1]benzothieno[2,3-e]-1,2-thiazine-3-carboxamide 1,1-dioxide (0.7 g).

mp: 244° C. (dec.).

IR (Nujol): 3200, 1490, 1470, 1360 cm$^{-1}$

NMR (DMSO-$d_6$, δ): 3.07 (3H, s), 7.23–9.06 (9H, m)

Analysis Calcd.: for $C_{19}H_{14}N_2O_5S_2 \cdot 0.3H_2O$: Calcd.: C, 54.27; H, 3.52; N, 6.66. Found: C, 53.83; H, 3.59; N, 6.56.

EXAMPLE 5

A solution of 2,7-dimethyl-4-hydroxy-3-methoxycarbonyl-2H-thieno[2,3-e]-1,2-thiazine, 1,1-dioxide (0.6 g) and 2-aminotropone (0.29 g) in xylene (15 ml) was refluxed for 6 hours and the reaction mixture was allowed to stand at ambient temperature.

The crystalline precipitates were collected by filtration and recrystallized from a mixture of chloroform and methanol to give 2,7-dimethyl-4-hydroxy-N-(1-oxo-2,4,6-cycloheptatrien-2-yl)-2H-thieno[2,3-e]-1,2-thiazine-3-carboxamide 1,1-dioxide (0.06 g).

mp: 229°–233° C.

IR (Nujol): 3220, 1640, 1615, 1560, 1490, 1388 cm$^{-1}$

Analysis Calcd. for $C_{16}H_{14}N_2O_5S_2$: Calcd.: C, 50.78; H, 3.73; N, 7.40. Found: C, 50.23; H, 3.83; N, 7.39.

EXAMPLE 6

A solution of 4-hydroxy-3-methoxycarbonyl-2H-thieno-[2,3-e]-1,2-thiazine 1,1-dioxide (0.7 g) and 2-aminotropone (0.341 g) in xylene (7 ml) was refluxed for 21 hours and the reaction mixture was allowed to stand at ambient temperature.

The crystalline precipitates were collected by filtration, washed with toluene and recrystallized from tetrahydrofuran to give 4-hydroxy-N-(1-oxo-2,4,6cycloheptatrien-2-yl)-2H-thieno[2,3-e]-1,2-thiazine-3-carboxamide 1,1-dioxide (0.47 g).

mp: 230° C. (dec.).

IR (Nujol): 3260, 1550, 1500, 1450, 1400, 1340, 1180 cm$^{-1}$

NMR (DMSO-d$_6$, δ): 7.00–7.47 (5H, m), 7.57 (1H, d, J=5 Hz), 8.17 (1H, d, J=5 Hz), 8.89 (1H, d, J=9 Hz), 10.53 (1H, brs).

EXAMPLE 7

4-Cinnamoyloxy-2-methyl-N-(1-oxo-2,4,6-cycloheptatrien-2-yl)-2H-thieno[2,3-e]-1,2-thiazine-3-carboxamide 1,1-dioxide was obtained according to a similar manner to that of Example 1.

mp: 167°–170° C.

NMR (DMSO-d$_6$, δ): 3.17 (3H, s) 6.96 (1H, d, J=16 Hz), 7.0–8.3 (12H, m), 8.90 (1H, d, J=9 Hz), 10.56 (1H, s).

Analysis Calcd. for $C_{24}H_{18}N_2O_6S_2$: Calcd.: C, 58.29; H, 3.67; N, 5.66. Found: C, 58.51; H, 3.72; N, 5.64.

EXAMPLE 8

To a mixture of 4-hydroxy-2-methyl-N-(1-oxo-2,4,6-cycloheptatrien-2-yl)-2H-thieno[2,3-e]-1,2-thiazine-3-carboxamide 1,1-dioxide (1.3 g) and cinnamoyl chloride (1.03 g) in N,N-dimethylformamide (19 ml) was added pyridine (0.59 ml) at 5° C. The mixture was stirred at 5° C. for 3 hours and then at ambient temperature for further 1.5 hours. The reaction mixture was poured into cold water (160 ml) to give crystals, which were collected by filtration and washed with water. Crude crystals were dissolved in chloroform and the organic layer was washed twice with water and brine, dried over anhydrous magnesium sulfate, treated with activated charcoal and evaporated under reduced pressure to give a crystalline residue.

The residue was subjected to column chromatography on silica gel (30 g) and eluted with methylene chloride to give crystals. Recrystallization from a mixture of ethyl acetate and hexane gave 4-cinnamoyloxy-2-methyl-N-(1-oxo-2,4,6-cycloheptatrien-2-yl)-2H-thieno[2,3-e]-1,2-thiazine-3-carboxamide 1,1-dioxide (0.56 g).

mp: 167°–170° C.

NMR (DMSO-d$_6$, δ): 2.17 (3H, s), 6.96 (1H, d, J=16 Hz), 7.0–8.3 (12H, m), 8.90 (1H, d, J=9 Hz), 10.56 (1H, s).

Analysis Calcd. for $C_{24}H_{18}N_2O_6S_2$: Calcd.: C, 58.29; H, 3.67; N, 5.66. Found: C, 58.51; H, 3.72; N, 5.64.

EXAMPLE 9

To a suspension of 4-cinnamoyloxy-2-methyl-N-(1-oxo-2,4,6-cycloheptatrien-2-yl)-2H-thieno[2,3-e]-1,2-thiazine-3-carboxamide 1,1-dioxide (0.49 g) in methanol (50 ml) was added dropwise 1N aqueous solution of sodium hydroxide (1.5 ml) at ambient temperature. The resultant mixture was stirred at the same temperature for 8 hours. After neutralization with 1N hydrochloric acid, the solvent was removed under reduced pressure. The residue was washed with water and dried up. The crude crystals were recrystallized from N,N-dimethylformamide to give 4-hydroxy-2-methyl-N-(1-oxo-2,4,6-cycloheptatrien-2-yl)-2H-thieno[2,3-e]-1,2-thiazine-3-carboxamide 1,1-dioxide (0.15 g).

mp: 242°–245° C.

IR (Nujol): 3220, 1615, 1560, 1510 cm$^{-1}$

Analysis Calcd. for $C_{15}H_{12}N_2O_5S_2$: Calcd. C, 49.44; H, 3.32; N, 7.69. Found: C, 49.17; H, 3.34; N, 7.68.

EXAMPLE 10

4-Hydroxy-2-methyl-N-(5-chloro-1-oxo-2,4,6-cycloheptatrien-2-yl)-2-H-thieno[2,3-e]-1,2-thiazine-3-carboxamide 1,1-dioxide was obtained according to a similar manner to that of Example 9.

mp: 243°–245° C.

IR (Nujol): 3260, 1645, 1605, 1560, 1510, 1350 cm$^{-1}$

Analysis Calcd. for $C_{15}H_{11}ClN_2O_5S_2$: Calcd.: C, 45.17; H, 2.78; N, 7.02. Found: C, 45.07; H, 3.01; N, 7.04.

EXAMPLE 11

4-Hydroxy-2-methyl-N-(2-hydroxy-1-oxo-2,4,6-cycloheptatrien-5-yl)-2H-thieno[2,3-e]-1,2-thiazine-3-carboxamide 1,1-dioxide was obtained according to a similar manner to that of Example 9.

mp: 231°–232° C.

IR (Nujol): 3600, 3350, 3250, 1645, 1605, 1530, 1200 cm$^{-1}$

NMR (NaOD+D$_2$O+CD$_3$OD, δ): 3.00 (3H, s), 7.0–7.8 (6H, m)

Analysis Calcd. for $C_{15}H_{12}N_2O_6S_2 \cdot 0.5H_2O$: Calcd.: C, 46.27; H, 3.62; N, 7.19. Found: C, 46.16; H, 3.63; N, 7.31.

EXAMPLE 12

4-Hydroxy-2-methyl-N-(1-oxo-2,4,6-cycloheptatrien-2-yl)-2H-[1]benzothieno[2,3-e]-1,2-thiazine-3-carboxamide 1,1-dioxide was obtained according to a similar manner to that of Example 9.

mp: 244° C. (dec.)

IR (Nujol): 3200, 1490, 1470, 1360 cm$^{-1}$

NMR (DMSO-d$_6$, δ): 3.07 (3H, s), 7.23–9.06 (9H, m)

Analysis Calcd. for $C_{19}H_{14}N_2O_5S_2 \cdot 0.3H_2O$: Calcd.: C, 54.27; H, 3.52; N, 6.66. Found: C, 53.83; H, 3.59; N, 6.56.

EXAMPLE 13

2,7-Dimethyl-4-hydroxy-N-(1-oxo-2,4,6-cycloheptatrien-2-yl)-2H-thieno[2,3-e]-1,2-thiazine-3-carboxamide 1,1-dioxide was obtained according to a similar manner to that of Example 9.

mp: 229°–223° C.

IR (Nujol): 3220, 1640, 1615, 1560, 1490, 1388 cm$^{-1}$

Analysis Calcd. for $C_{16}H_{14}N_2O_5S_2$: Calcd.: C, 50.78; H, 3.73; N, 7.40. Found: C, 50.23; H, 3.83; N, 7.39.

EXAMPLE 14

4-hydroxy-N-(1-oxo-2,4,6-cycloheptatrien-2-yl)-2H-thieno[2,3-e]-1,2-thiazine-3-carboxamide 1,1-dioxide was obtained according to a similar manner to that of Example 9.

mp: 230° C. (dec.).

IR (Nujol): 3260, 1550, 1500, 1450, 1400, 1340, 1180 cm$^{-1}$

NMR (DMSO-d$_6$, δ): 7.00–7.47 (5H, m), 7.57 (1H, d, J=5 Hz), 8.17 (1H, d, J=5 Hz), 8.89 (1H, d, J=9 Hz), 10.53 (1H, brs)

What we claim is:

1. A compound of the formula:

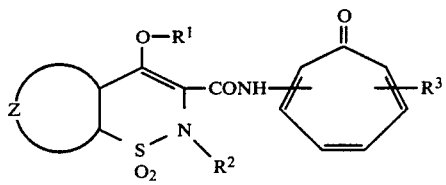

wherein
- R$^1$ is hydrogen, lower alkanyol, aroyl or ar(lower)alkenoyl,
- R$^2$ is hydrogen or lower alkyl,
- R$^3$ is hydrogen, hydroxy, halogen, lower alkyl or lower alkoxy,
- Z is taken together with the adjacent carbon atoms to form an unsaturated heterocyclic ring selected from the group consisting of furan, thiophene, pyrrole, imidazole, pyridine, benzofuran, benzothiophene, indole and quinoline, which may be substituted with phenyl, halogen, lower alkanoyl or lower alkyl, and the heavy solid line means single or double bond, and pharmaceutically acceptable salts thereof.

2. A compound of claim 1, wherein R$^1$ is hydrogen.

3. A compound of claim 2, wherein R$^3$ is hydrogen, hydroxy or halogen.

4. A compound of claim 3, wherein R$^2$ is methyl.

5. A compound of claim 4, which is 4-hydroxy-2-methyl-N-(1-oxo-2,4,6-cycloheptatrien-2-yl)-2H-thieno[2,3-e]-1,2-thiazine-3-carboxamide 1,1-dioxide.

6. A compound of claim 4, which is 4-hydroxy-2-methyl-N-(1-oxo-2,4,6-cycloheptatrien-2-yl)-2H-[1]benzothieno[2,3-e]-1,2-thiazine-3-carboxamide 1,1-dioxide.

7. A compound of claim 4, which is 4-hydroxy-2-methyl-N-(2-hydroxy-1-oxo-2,4,6-cycloheptatrien-5-yl)-2H-thieno[2,3-e]-1,2-thiazine-3-carboxamide 1,1-dioxide.

8. A compound of claim 1, wherein R$^1$ is lower alkanoyl, arroyl or ar(lower)alkenoyl.

9. A compound of claim 1, wherein R$^1$ is ar(lower)alkenoyl.

10. An antiinflammatory, antirheumatic pharmaceutical composition comprising an effective amount of a compound of claim 1, as an effective ingredient, in association with a pharmaceutically acceptable, substantially nontoxic carrier or excipient.

11. A method for treatment of inflammation which comprises administering an effective amount of a compound of claim 1 to human beings or animals.

12. A method for treatment of rheumatism which comprises administering an effective amount of a compound of claim 1 to human beings or animals.

* * * * *

UNITED STATES PATENT AND TRADEMARK OFFICE
CERTIFICATE OF CORRECTION

PATENT NO. : 4,563,453

DATED : January 7, 1986

INVENTOR(S) : IKUO UEDA ET AL

It is certified that error appears in the above-identified patent and that said Letters Patent is hereby corrected as shown below:

In the following locations:

Abstract, line 2;

Col.1, lines 35 and 55 (two occurrences);

Col.2, lines 10, 35 and 45;

Col. 3, lines 5, 15 and 26; and

Col. 11, line 15;

the partial structure of the formula: 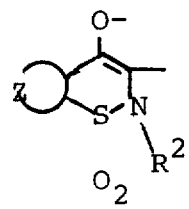

should read:

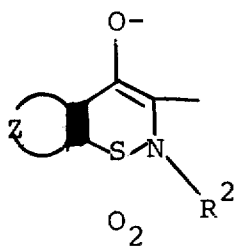

UNITED STATES PATENT AND TRADEMARK OFFICE
CERTIFICATE OF CORRECTION

PATENT NO. : 4,563,453

DATED : January 7, 1986

INVENTOR(S) : IKUO UEDA ET AL

It is certified that error appears in the above-identified patent and that said Letters Patent is hereby corrected as shown below:

Col. 11, line 23, "alkanyol", should read

-- alkanoyl --.

Signed and Sealed this

Seventh Day of October, 1986

[SEAL]

Attest:

DONALD J. QUIGG

Attesting Officer

Commissioner of Patents and Trademarks